United States Patent [19]

Suzukamo et al.

[11] Patent Number: 4,788,323

[45] Date of Patent: Nov. 29, 1988

[54] METHOD FOR RACEMIZATION OF OPTICALLY ACTIVE CHRYSANTHEMIC ACID OR ITS ESTER

[75] Inventors: Gohfu Suzukamo, Osaka; Yoji Sakito, Hyogo; Masami Fukao, Shiga; Koji Hagiya, Osaka, all of Japan

[73] Assignee: Sumitomo Chemical Company, Limited, Osaka, Japan

[21] Appl. No.: 93,234

[22] Filed: Sep. 4, 1987

[30] Foreign Application Priority Data

Sep. 4, 1986 [JP]  Japan ................................. 61-208768
Feb. 10, 1987 [JP] Japan ................................. 62-28581
Feb. 10, 1987 [JP] Japan ................................. 62-28582

[51] Int. Cl.$^4$ ........................................... C07C 69/747
[52] U.S. Cl. ............................... 560/124; 562/506; 562/401
[58] Field of Search ................. 560/124; 562/401, 506

[56] References Cited

U.S. PATENT DOCUMENTS

| | | | |
|---|---|---|---|
| 3,282,984 | 11/1966 | Matsui et al. | 260/468 |
| 3,657,086 | 4/1972 | Matsui et al. | 204/158 |
| 3,794,680 | 2/1974 | Matsui | 562/506 |
| 3,989,750 | 11/1976 | Nagase et al. | 260/544 C |
| 4,182,906 | 1/1980 | Suzukamo et al. | 562/506 |
| 4,473,703 | 9/1984 | Suzukamo | 560/124 |
| 4,485,257 | 11/1984 | Suzukamo et al. | 562/401 |
| 4,644,080 | 2/1987 | Suzukamo et al. | 560/124 |
| 4,659,864 | 4/1987 | Suzukamo et al. | 560/124 |

FOREIGN PATENT DOCUMENTS

| | | |
|---|---|---|
| 0155765 | 9/1985 | European Pat. Off. . |
| 0165070 | 12/1985 | European Pat. Off. . |
| 49-31978 | 8/1974 | Japan ................................. 562/506 |
| 50-88055 | 7/1975 | Japan ................................. 562/506 |

Primary Examiner—Michael L. Shippen
Attorney, Agent, or Firm—Birch, Stewart, Kolasch & Birch

[57] ABSTRACT

Racemization of optically active chrysanthemic acid or its ester of the formula:

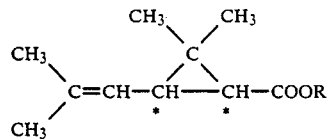

wherein R represents a hydrogen atom or an alkyl, cycloalkyl or aralkyl group of 1–20 carbon atoms and * indicates an asymmetric carbon atom, is effected by contacting it with hydrogen bromide or a phosphorus bromide compound. This method may also be effected in the presence of a peroxide or an azo compound. This method is industrially very useful.

30 Claims, No Drawings

METHOD FOR RACEMIZATION OF OPTICALLY ACTIVE CHRYSANTHEMIC ACID OR ITS ESTER

The present invention relates to a method for the racemization of chrysanthemic acid or its ester. More particularly, it relates to a method for the racemization of optically active chrysanthemic acid or its ester of the formula:

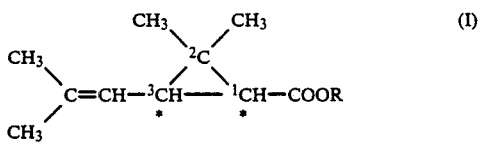

(wherein R represents a hydrogen atom, an alkyl group of 1–20 carbon atoms, a cycloalkyl group of 3–20 carbon atoms or an aralkyl group of 7–20 carbon atoms and * mark indicates an asymmetric carbon atom), which comprises contacting the acid or its ester with hydrogen bromide or a phosphorus bromide compound in the presence or absence of a peroxide or an azo compound.

Chrysanthemic acid constitutes an acid component of esters well-known as so-called pyrethroidal insecticides, such as pyrethrin, allethrin, phthalthrin, etc., which are utilized as low mammalian toxic, quickly effective insecticides, and the chrysanthemic acid or its ester represented by the above formula (I) is useful as intermediates of these esters.

The chrysanthemic acid represented by the above formula (I) has four isomers, that is, two geometrical isomers, i.e. cis and trans forms, which respectively have two optical isomers, i.e. (+) and (−) forms. It has been known that, in general, among the isomers the esters composed of trans-form acid exhibit stronger insecticidal activity than those composed of the corresponding cis-form acid, and furthermore, the esters composed of (+)-form acid exhibit exceedingly higher activity than those composed of the corresponding (−)-isomer.

In general, chrysanthemic acid is industrially produced as a mixture of cis and trans forms, each of which is in the form of a racemic mixture, namely, as (±)-form. Optical resolution of the thus-synthesized acid by means of an optically active organic base is conducted to obtain the (+)-form acid which is utilized for the preparation of insecticidal compounds with a higher activity. Wherein, the remaining (−)-isomer after the optical resolution is of little use, since the esters composed thereof are almost inactive. Accordingly, it is a problem to be solved in the production of the (+)-form acid, particularly in a commercial scale, that the (−)-form acid should be racemized with a high efficiency, so as to be utilized again as the material for the optical resolution mentioned above.

Racemization of optically active chrysanthemic acid represented by the formula (I) is difficult, since it possesses two asymmetric carbon atoms exhibited by * marks, as shown above, at the 1- and 3-positions.

Some methods for racemization have so far been studied. The methods known include a method in which (−)-trans-chrysanthemic acid is oxydized at its $C_3$-substituted isobutenyl group to convert to a ketoalcohol group, and the acid group at the $C_1$-position is converted to a lower alkyl ester, which is then subjected to a reaction with an alkali metal alcoholate in a solvent (U.S. Pat. No. 3,282,984); a method in which (−)-trans-chrysanthemic acid is irradiated with ultraviolet rays in the presence of a photosensitizer (U.S. Pat. No. 3,657,086). The former requires many reaction steps and the latter is inferior in reactivity and besides consumes a large quantity of electric power of light source and the life of light source is relatively short. Thus, there are various problems in industrial application.

The inventors proposed the following methods; a method in which optically active chrysanthemic acid is converted to the corresponding acid halide and then is brought into contact with a Lewis acid (U.S. Pat. Nos. 3,989,750 and 4,182,906); a method in which optically active chrysanthemic acid is converted to acid anhydride and then is brought into contact with iodine (U.S. Pat. No. 4,485,257); and a method in which chrysanthemic acid is allowed to contact with a specific catalyst, boron bromide or aluminum bromide in the presence or absence of a peroxide (U.S. Pat. Nos. 4,644,080 and 4,659,864).

After an extensive study, the inventors have now found that optically active chrysanthemic acid or its ester of the formula (I) is able to racemize conveniently and in high yield by a treatment with a hydrogen bromide or a phosphorus bromide compound and the racemization proceeds more efficiently in the presence of an azo compound and a peroxide. This invention is established on the basis of such finding and additional research.

According to the present invention, more common and inexpensive hydrogen bromide and phosphorus bromide compound can be used and the optically active chrysanthemic acid or its ester is able to be racemized readily and in high yield and the method of the present invention is very convenient for racemization, particularly, in a commercial scale. Moreover, the present invention enables direct utilization, with high efficiency, of (−)-chrysanthemic acid or its ester, which is separated off in the procedures of optical resolutions, without converting into other derivatives.

The racemic mixture obtained by the method of the present invention is rich in trans isomer which is more effective and the method is also advantageous in this respect.

Further, the method of the present invention can also be used for the conversion of racemic cis isomer or a racemic mixture of cis and trans isomers of chrysanthemic acid into the corresponding racemic trans-rich isomer.

The method of the present invention will more fully be described hereinafter.

In the present invention, any of the four optical isomers of chrysanthemic acid or its ester is able to be used solely or in mixtures of isomers as the starting material. Namely, the starting material of any degree of the optical purity is employed. Needless to say, however, it is preferred to use, as the starting material, (−)-form or one rich in the (−)-form.

As the optically active chrysanthemic acid or ester represented by the formula (I) mention may be made of, for example, chrysanthemic acid, methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

Hydrogen bromide used in the present invention may be in a gaseous form or in the form of solution in a solvent and, if necessary, may be produced in the reaction system using a bromide such as lithium bromide, sodium bromide or potassium bromide with an acid such as sulfuric acid. Any solvents may be used for hydrogen bromide as far as they do not inhibit the racemization reaction and as examples thereof, mention may be made of organic solvents such as carboxylic acids, saturated hydrocarbons, aromatic hydrocarbons, halogenated saturated hydrocarbons, halogenated aromatic hydrocarbons, etc. and water.

The phosphorus bromide compounds used in the present invention include, for example, compounds of bromine and phosphorus such as phosphorus tribromide, phosphorus pentabromide and phosphorus oxytribromide and mixtures thereof.

Hydrogen bromide or phosphorus bromide compound is used generally in an amount of 1/1000–¼ mol, preferably 1/20–¼ mol when used alone and 1/200–1/5 mol when used in the presence of peroxide or azo compound, per mol of chrysanthemic acid or ester.

As examples of the peroxides, mention may be made of hydroperoxides such as t-butyl hydroperoxide, 1,1,3,3-tetramethylbutyl hydroperoxide, cumene hydroperoxide, diisopropylbenzene hydroperoxide, etc., hydroperoxides produced by oxidation of ethers such as tetrahydrofuran, dioxane, etc., diacyl peroxides such as benzoyl peroxide, lauroyl peroxide, etc., peroxy esters such as t-butyl perbenzoate, t-butyl peracetate, diisopropyl peroxydicarbonate, dicyclohexyl peroxydicarbonate, etc., ketone peroxides such as methyl ethyl ketone peroxide, cyclohexanone peroxide, etc., dialkyl peroxides such as di-t-butyl peroxide, dicumyl peroxide, etc., peracids such as peracetic acid, etc., hydrogen peroxide, etc. Of these peroxides, preferred are hydroperoxides, diacyl peroxides and peroxy esters and more preferred are hydroperoxides.

The peroxide is used generally in an amount of 1/20–5 mols, preferably 1/10–2 mols per mol of hydrogen bromide or phosphorus bromide compound.

Azo compound to be employed includes azonitriles such as azobisisobutylonitrile, 2,2'-azobis(2,4-dimethylvaleronitrile), 1,1'-azobis(cyclohexane-1-carbonitrile), 4,4'-azobis-4-cyanopentanoic acid, 2-phenylazo-2,4-dimethyl-4-methoxyvaleronitrile and 2-cyano-2-propylazoformamide; azoesters such as methyl azobisisobutyrate and ethyl azobisisobutyrate and alkylazo compounds such as azo-t-butane. Azo-nitriles and azo-esters are preferable.

The azo compound is used, in general, in such an amount as from 1/10 to 5 mol, preferably ¼ to 2 mol, based upon a mol of the hydrogen bromide or the phosphorus bromide compound employed.

The present racemization reaction is preferably carried out in the presence of an inert solvent. The solvents include saturated aliphatic hydrocarbons, aromatic hydrocarbons and their halide compounds, ethers, etc.

Reaction temperature varies depending on the hydrogen bromide, phosphorus bromide compound, peroxide and azo compound employed. The temperature ranges usually from −30° C. to the boiling point of the chrysanthemic acid or its ester or the boiling point of the solvent when it is employed. Temperature is usually −20° C. to 100° C.

The reaction time varies depending on the amounts of hydrogen bromide, phosphorus bromide compound and peroxide or of an azo compound and reaction temperature, too, but usually ranges from a few minutes to 10 hours.

In carrying out the method of the present invention, for example, when using peroxide or azo compound, the chrysanthemic acid is mixed with the peroxide or azo compound in the presence of a solvent then thereto is added the hydrogen bromide or phosphorus bromide compound; or the chrysanthemic acid to be treated is dissolved in a solvent and then thereinto are added in parallel peroxide or azo compound and hydrogen bromide or phosphorus bromide compound.

When an aqueous hydrobromic acid solution as hydrogen bromide and an organic solvent immiscible with water as a reaction solvent such as aromtic hydrocarbon are used, the desired reaction can be more smoothly progressed in the presence of an inorganic salt or the like which has high solubility in water and does not inhibit the reaction in the reaction system. As the inorganic salt, mention may be made of, for example, lithium bromide, lithium chloride, calcium bromide, calcium chloride, magnesium bromide, magnesium chloride, magnesium sulfate, phosphorus pentoxide, etc. The desired reaction can further smoothly progress by adding an organic solvent miscible with water and inert to hydrogen bromide, e.g., acetic acid, dioxane, etc. to the aqueous hydrobromic acid solution.

The proceeding of the reaction can be checked by measurement of the optical rotation, gas-chromatography, etc.

The racemized chrysanthemic acid or ester thus obtained can be reused as a starting material for optical resolution or as an intermediate for insecticidal esters.

The following nonlimiting examples will further explain the present invention.

EXAMPLE 1

In a 50 ml flask were charged 10.0 g of chrysanthemic acid (composition: (+)-cis, 1.8%; (−)-cis, 18.3%; (+)-trans, 11.1%; (−)-trans, 68.8%), 15.0 g of toluene and 0.13 g of tert-butyl hydroperoxide under a nitrogen atmosphere. Thereto was added dropwise 0.44 g of phosphorus tribromide with stirring at 20° C. and stirring was continued for 1 hour at this temperature. After the reaction, the reaction mixture was washed with water and to the resulting organic layer was added 28.6 g of 10% aqueous sodium hydroxide solution, followed by stirring with heating at about 40° C.

The separated aqueous layer was neutralized with dilute sulfuric acid and extracted with toluene and then the toluene layer was washed with water. This toluene solution was concentrated and then distilled to obtain 9.6 g of distillate having a boiling point of 110°–119° C./2.5 mmHg. The IR spectrum of the product was identical with that of chrysanthemic acid. A part of the distillate was converted to (+)-2-octyl ester, which was subjected to measurement of the optical isomer ratio by gas chromatography to give the following results: (+)-cis, 2.5%; (−)-cis, 2.5%; (+)-trans, 47.0%; and (−)-trans, 48.0%.

EXAMPLE 2

In a 50 ml flask were charged 5.0 g of the same chrysanthemic acid as used in Example 1, 10 g of dioxane and 0.11 g of cumene hydroperoxide under a nitrogen atmosphere. Thereto was added dropwise 0.22 g of phosphorus tribromide with stirring at 20° C., followed by stirring at this temperature for 1 hour. After the reaction, 4.5 g of 40% aqueous sodium hydroxide solution was added to the reaction mixture and the solvent was distilled out under reduced pressure. To the residue were added water and toluene to effect extraction to separate an aqueous layer. This aqueous layer was neutralized with dilute sulfuric acid and extracted with toluene and then the organic layer was washed with water. Then, the organic layer was concentrated and then distilled to obtain 4.8 g of a distillate having a boiling point of 110°–119° C./2.5 mmHg.

A part of the distillate was subjected to measurement of optical isomer ratio in the same manner as in Example 1 to give the following results: (+)-cis, 2.4%; (−)-cis, 2.5%, (+)-trans, 47.0%; and (−)-cis, 48.1%.

EXAMPLE 3

In a 50 ml flask were charged 5.0 g of ethyl ester of chrysanthemic acid (composition: (+)-cis, 1.8%, (−)-cis, 18.3%, (+)-trans, 11.1%, (−)-trans, 68.8%), 20 g of dioxane and 0.07 g of tert-butyl hydroperoxide. Thereto was added dropwise 0.21 g of phosphorus tribromide with stirring at 20° C., followed by stirring for 0.5 hours. After the reaction, 2% aqueous sodium hydroxide solution was added to carry out neutralization and the solvent was distilled out under reduced pressure. To the residue were added hexane and 2% aqueous sodium hydroxide solution to carry out extraction and the organic layer was washed with water. The resulting organic layer was concentrated under reduced pressure and then was distilled to obtain 4.6 g of distillate having a boiling point of 85°–88° C./10 mmHg.

The IR spectrum of the product showed that this was ethyl ester of chrysanthemic acid. A part of the distillate was hydrolyzed by a conventional method and the resulting carboxylic acid was converted to an ester with (+)-2-octanol, which was subjected to a determination of its optical isomer ratio by gas chromatography to give the following results: (+)-cis, 2.3%; (−)-cis, 2.4%; (+)-trans, 47.0%; and (−)-trans, 48.3%.

EXAMPLE 4

In a 35 ml flask were charged 1.0 g of (−)-cis-chrysanthemic acid, 19.0 g of dioxane and 0.034 g of 60% aqueous hydrogen peroxide under nitrogen atmosphere. Thereto was added dropwise 0.32 g of phosphorus tribromide with stirring at 20° C., followed by stirring for 0.5 hours at this temperature.

After the reaction, a part of the reaction mixture was taken and converted to (+)-2-octyl ester, which was subjected to a determination of its optical isomer ratio of the chrysanthemic acid to give the following results: (+)-cis, 2.7%; (−)-cis, 4.0%; (+)-trans, 45.6%; and (−)-trans, 47.7%.

EXAMPLE 5

In a 35 ml flask were charged 2.0 g of the same chrysanthemic acid as used in Example 1, 18.0 g of toluene and 0.20 g of benzoyl peroxide under a nitrogen atmosphere. Thereto was added dropwise 0.23 g of phosphorus tribromide with stirring at 80° C., followed by stirring for 0.5 hours at this temperature.

After the reaction, a determination of the optical isomer ratio was effected in the same manner as in Example 4 to obtain the following results: (+)-cis, 3.7%; (−)-cis, 3.6%; (+)-trans, 46.1%; and (−)-trans 46.6%.

EXAMPLE 6

In a 35 ml flask were charged 2.0 g of the same crysanthemic acid used in Example 1, 18.0 g of dioxane and 0.23 g of tert-butyl perbenzoate under a nitrogen atmosphere. Thereto was added dropwise 0.64 g of phosphorus tribromide with stirring at 80° C. and stirring was carried out for 0.5 hours at this temperature.

After the reaction, a determination of the optical isomer ratio was effected in the same manner as in Example 4 to obtain the following results: (+)-cis, 4.6%; (−)-cis, 4.5%; (+)-trans, 43.5%; and (−)-trans, 47.4%.

EXAMPLE 7

In a 35 ml flask were charged 2.0 g of the same ethyl ester of chrysanthemic acid as used in Example 3, 18.0 g of carbon tetrachloride and 0.065 g of tert-butyl hydroperoxide under nitrogen atmosphere. Thereto was added dropwise 0.19 g of phosphorus tribromide with stirring at 0° C. and stirring was effected for 1 hour at this temperature.

After the reaction, a part of the reaction mixture was treated in the same manner as in Example 3 and a determination of the optical isomer ratio was effected to obtain the following results: (+)-cis, 2.0%; (−)-cis, 1.9%; (+)-trans, 47.2%; and (−)-trans, 48.9%.

EXAMPLE 8

In a 35 ml flask were charged 0.5 g of (−)-cis-chrysanthemic acid, 5 g of dioxane and 26 mg of tert-butyl hydroperoxide under a nitrogen atmosphere. Thereto was added dropwise 0.12 g of phosphorus pentabromide with stirring at 20° C. and this was stirred for 0.5 hours at this temperature.

After the reaction, in the same manner as in Example 1, a part of the reaction mixture was treated and a determination of the optical isomer ratio was effected to obtain the following results: (+)-cis, 2.0%; (−)-cis, 2.6%; (+)-trans, 46.6%; and (−)-trans, 48.8%.

EXAMPLE 9

In a 35 ml flask were charged 0.5 g of (−)-cis-chrysanthemic acid, 5 g of dioxane and 60 mg of tert-butyl perbenzoate under a nitrogen atmosphere. Thereto was added dropwise 0.12 g of phosphorus oxybromide with stirring at 80° C., followed by stirring for 0.5 hours at this temperature.

After the reaction, the reaction mixture was treated in the same manner as in Example 1 and a determination of optical isomer ratio was effected to obtain the following results: (+)-cis, 2.6%; (−)-cis, 2.7%; (+)-trans, 46.4%; and (−)-trans, 48.3%.

EXAMPLE 10

1.78 g of (−)-chrysanthemic acid (composition: (+)-cis, 1.8%; (−)-cis, 17.6%; (+)-trans, 10.1%; and (−)-trans, 70.5%) was dissolved in 10 ml of benzene, followed by addition of 43 mg of azobisisobutyronitrile. Thereto was added dropwise a solution of phosphorus tribromide (144 mg) in benzene with stirring at 80° C. over a period of 15 minutes.

After the reaction, the reaction mixture was treated in the same manner as in Example 1 to obtain 1.51 g of chrysanthemic acid having a boiling point of 110°–119° C./2.5 mmHg.

By a usual method, optical isomer ratio in the chrysanthemic acid was determined to obtain the following results: (+)-cis, 2.5%; (−)-cis, 2.5%; (+)-trans, 47.2%; and (−)-trans, 47.8%.

EXAMPLE 11

1.26 g of the same (−)-chrysanthemic acid as used in Example 10 was dissolved in 10 ml of benzene, followed by addition of 50 mg of azobisisobutyronitrile. Then, thereto was added dropwise a solution of phosphorus pentabromide (220 mg) in benzene with stirring at 70° C. over a period of 15 minutes.

Thereafter, the procedure of Example 1 was carried out to obtain 1.01 g of chrysanthemic acid.

Optical isomer ratio in the chrysanthemic acid was as follows: (+)-cis, 4.1%; (−)-cis, 4.1%; (+)-trans, 43.9%; and (−)-trans, 47.9%.

EXAMPLE 12

2.12 g of the same (−)-chrysanthemic acid as used in Example 10 was dissolved in 10 ml of benzene. To the solution was added 92 mg of methyl azobisisobutyrate, followed by heating to 70° C. Then, thereto was added dropwise a solution of phosphorus tribromide (171 mg) in benzene over a period of 15 minutes.

Thereafter, the same procedure as in Example 1 was effected to obtain 1.73 g of chrysanthemic acid.

Optical isomer ratio was as follows: (+)-cis, 3.6%; (−)-cis, 3.5%; (+)-trans, 45.2%; and (−)-trans, 47.7%.

EXAMPLE 13

3.48 g of (−)-ethyl chrysanthemate (composition: (+)-cis, 2.5%; (−)-cis, 14.8%; (+)-trans, 11.9%; and (−)-trans, 70.8%) was dissolved in 20 ml of benzene, followed by addition of 100 mg of azobisisobutyronitrile. Thereto was added dropwise a solution of phosphorus pentabromide (540 mg) in benzene with stirring at 80° C. over 30 minutes.

After the reaction, ice water was added to the reaction mixture and stirred to decompose the catalyst. After removal of an aqueous layer, the organic layer was subjected to distillation under reduced pressure to remove the solvent. The residue was refluxed under heating for 3 hours together with 20 g of 10% aqueous sodium hydroxide solution and then toluene was added to remove neutral matters as a toluene layer. The aqueous layer was acidified with hydrochloric acid and extracted with toluene. The organic layer was washed with water and dried over anhydrous sodium sulfate. The solvent was distilled out under reduced pressure and the residue was distilled to obtain 2.49 g of a distillate having a boiling point of 110°–119° C./2.5 mmHg. The IR spectrum of the product showed that this was chrysanthemic acid.

Optical isomer ratio of the chrysanthemic acid was as follows: (+)-cis, 3.9%; (−)-cis, 3.2%; (+)-trans, 43.3%; and (−)-trans, 49.6%.

EXAMPLE 14

In a 20 ml flask were charged 1.0 g of (+)-cis chrysanthemic acid and 9 g of toluene, followed by adding dropwise 0.24 g of phosphorus tribromide with stirring at 20° C. After stirring for 1 hour at this temperature, optical isomer ratio of the reaction mixture was determined to obtain the following results: (+)-cis, 6.9%; (−)-cis, 4.8%; (+)-trans, 44.6%; and (−)-trans, 43.7%.

EXAMPLE 15

25.0 g of (−)-chrysanthemic acid (composition: (+)-cis, 3.0%; (−)-cis, 18.8%; (+)-trans, 10.2%; and (−)-trans, 68.0%) was dissolved in 38 ml of toluene. To the solution with stirring were added in parallel 3.04 g of 25% solution of hydrogen bromide in acetic acid and a solution of t-butyl hydroperoxide (0.23 g) in toluene with stirring at room temperature over a period of 30 minutes.

After the reaction, the reaction mixture was treated as in Example 1 to obtain 24.0 g of chrysanthemic acid having a boiling point of 110°–119° C./2.5 mmHg. Optical isomer ratio was as follows: (+)-cis, 1.8%; (−)-cis, 2.4%; (+)-trans, 46.0%; and (−)-trans, 49.8%.

EXAMPLE 16

25.0 g of the same chrysanthemic acid as used in Example 15 was dissolved in 38 ml of toluene and therein was suspended 3.0 g of lithium bromide. Under stirring, thereto were added dropwise a solution of t-butyl hydroperoxide (0.44 g) in toluene and 2.23 g of 48% aqueous hydrobromic acid solution at 20° C. over a period of 30 minutes.

After the reaction, the reaction mixture was treated as in Example 1 to obtain 24.0 g of chrysanthemic acid. Optical isomer ratio was as follows: (+)-cis, 2.0%; (−)-cis, 2.0%; (+)-trans, 47.1%; and (−)-trans, 48.9%.

EXAMPLE 17

25.0 g of the same chrysanthemic acid as used in Example 15 was dissolved in 38 ml of toluene and therein was suspended 3.0 g of calcium chloride. With stirring, thereto were added dropwise a solution of t-butyl hydroperoxide (0.38 g) in toluene and 25.1 g of acetic acid solution of aqueous hydrobromic acid solution (composition: HBr 38.4%, acetic acid 20% and water 41.6%) at 20° C. over a period of 30 minutes.

After the reaction, the same treatment as in Example 1 was carried out to obtain 24.0 g of chrysanthemic acid. Optical isomer ratio was as follows: (+)-cis, 2.4%; (−)-cis, 2.4%; (+)-trans, 45.2%; and (−)-trans, 50.0%.

EXAMPLE 18

25 g of the same (−)-chrysanthemic acid as used in Example 15 was dissolved in 38 ml of toluene, followed by adding 0.75 g of t-butyl hydroperoxide. Into this solution with stirring was introduced 2.02 g of hydrogen bromide gas at room temperature over a period of 30 minutes.

Thereafter, the same treatment as in Example 1 was effected to obtain 22.4 g of chrysanthemic acid. Optical isomer ratio was as follows: (+)-cis, 2.3%; (−)-cis, 2.1%; (+)-trans, 44.3%; and (−)-trans, 51.3%.

EXAMPLE 19

1.04 g of the same (−)-chrysanthemic acid as used in Example 15 was dissolved in 5 ml of toluene, followed by adding 131 mg of benzoyl peroxide and then 430 mg of 25% solution of hydrogen bromide in acetic acid with stirring at 80° C. over a period of 3 minutes.

Thereafter, the same treatment as in Example 1 was effected to obtain 940 mg of chrysanthemic acid. Optical isomer ratio was as follows: (+)-cis, 4.7%; (−)-cis, 4.2%; (+)-trans, 40.9%; and (−)-trans, 50.2%.

EXAMPLE 20

2.00 g of the same (−)-chrysanthemic acid as used in Example 15 was dissolved in 20 ml of dioxane and then thereto was added 110 mg of t-butyl hydroperoxide, followed by adding dropwise 300 mg of 48% aqueous hydrogen bromide solution with stirring at room temperature.

Thereafter, the same treatment as in Example 2 was carried out to obtain 1.70 g of chrysanthemic acid.

Optical isomer ratio was as follows: (+)-cis, 2.3%; (−)-cis, 2.4%; (+)-trans, 44.7%; and (−)-trans, 50.6%.

EXAMPLE 21

2.23 g of (—)-ethyl chrysanthemate (composition: (+)-cis, 2.5%; (—)-cis, 14.8%; (+)-trans, 11.9%; and (—)-trans, 70.8%) was dissolved in 20 ml of dioxane and then 95 mg of azobisisobutyronitrile was added thereto, followed by adding dropwise a benzene solution of 370 mg of 25% acetic acid solution of hydrogen bromide with stirring at 80° C. over a period of 30 minutes.

After the reaction, the reaction mixture was neutralized with 2% aqueous sodium hydroxide solution and then the solvent was distilled out under reduced pressure. To the residue were added hexane and 2% aqueous sodium hydroxide solution to effect extraction and the organic layer was washed with water. The obtained organic layer was concentrated under reduced pressure and subjected to distillation to obtain 2.06 g of a distillate having a boiling point of 85°–88° C./10 mmHg.

The IR spectrum of the product showed that it was ethyl ester of chrysanthemic acid. A part of the product was hydrolyzed by a conventional method to obtain the carboxylic acid. Gas chromatography assay after conversion of the carboxylic acid to an ester with (+)-2-octanol gave the following results: (+)-cis, 3.0%, (—)-cis, 3.1%; (+)-trans, 46.3%; and (—)-trans, 47.6%.

EXAMPLE 22

2.50 g of the same (—)-ethyl chrysantemate as used in Example 21 was dissolved in 10 ml of dioxane and then 115 mg of t-butyl hydroperoxide was added thereto. Thereto was added with stirring 410 mg of 25% solution of hydrogen bromide in acetic acid at room temperature. Thereafter, the same treatment as in Example 21 was carried out to obtain 2.25 g of ethyl chrysanthemate.

Optical isomer ratio was as follows: (+)-cis, 2.5%; (—)-cis, 2.5%; (+)-trans, 47.1%; and (—)-trans, 47.9%.

EXAMPLE 23

2.84 g of the same (—)-chrysanthemic acid as used in Example 15 and 0.14 g of azobisisobutyronitrile were dissolved in 25 ml of benzene. To the solution was added 0.55 g of 25% solution of hydrogen bromide in acetic acid at 70° C. and reaction was carried out for 30 minutes.

Gas chromatography assay of the reaction mixture gave the following results: (+)-cis, 3.8%; (—)-cis, 3.8%; (+)-trans, 45.3%; and (—)-trans, 47.1%.

EXAMPLE 24

10.0 g of the same (—)-chrysanthemic acid as used in Example 15 was dissolved in 100 g of toluene. Thereto was added 4.82 g of a 25% solution of hydrogen bromide in acetic acid at 20° C. and stirring was effected for 1 hour.

Gas chromatography assay of the reaction mixture gave the following results: (+)-cis, 2.7%; (—)-cis, 3.6%; (+)-trans, 46.9%; and (—)-trans, 46.8%.

EXAMPLE 25

320 mg of the same (—)-ethyl chrysanthemate as used in Example 21 was dissolved in 4 ml of toluene. Thereto was added 52 mg of a 25% solution of hydrogen bromide in acetic acid at 20° C. and stirring was carried out for 30 minutes.

Optical isomer ratio was as follows: (+)-cis, 3.6%; (—)-cis, 3.6%; (+)-trans, 33.0%; and (+)-trans, 59.8%.

EXAMPLE 26

5.0 g of cis-chrysanthemic acid was dissolved in 15.0 g of dioxane, followed by adding dropwise 68 mg of t-butyl hydroperoxide and 150 mg of phosphorus tribromide at 20° C. and stirring for 30 minutes at this temperature.

After the reaction, 4.5 g of 40% aqueous sodium hydroxide solution was added to the reaction mixture and the solvent was distilled out under reduced pressure. To the residue were added water and toluene to effect extraction to separate the aqueous layer. This aqueous layer was neutralized with dilute sulfuric acid and extracted with toluene and then the organic layer was washed with water. This organic layer was concentrated and then distilled to obtain 4.8 g of crysanthemic acid having a boiling point of 110°–119° C./2.5 mmHg.

Gas chromatography assay of the product gave the composition of cis, 5.0% and trans, 95.0%.

EXAMPLE 27

0.50 g of cis-chrysanthemic acid and 26 mg of t-butyl hydroperoxide were dissolved in 5 ml of dioxane. Thereto was added 120 mg of phosphorus pentabromide at 20° C. and reaction was effected for 30 minutes.

Gas chromatography assay of the reaction mixture gave the following results: cis, 4.6% and trans, 95.4%.

EXAMPLE 28

0.50 g of cis-chrysanthemic acid and 30 mg of t-butyl hydroperoxide were dissolved in 5 ml of dioxane. Thereto was added 120 mg of phosphorus oxybromide at 80° C. and reaction was effected for 30 minutes. Gas chromatography assay of the reaction mixture gave the composition: cis, 5.2% and trans, 94.8%.

EXAMPLE 29

1.0 g of cis-chrysanthemic acid and 0.034 g of 60% aqueous hydrogen peroxide were dissolved in 19.0 g of dioxane. With stirring, to the solution was added dropwise 0.32 g of phosphorus tribromide at 20° C. and stirring was carried out for 0.5 hours at this temperature.

After the reaction, a part of the reaction mixture was taken and the isomer ratio was determined to yield: cis, 6.7% and trans, 93.3%.

EXAMPLE 30

5.0 g of cis-chrysanthemic acid was dissolved in 20 ml of dioxane, followed by adding dropwise 0.03 g of t-butyl hydroperoxide and 0.34 g of 25% HBr-acetic acid at 20° C. and stirring for 30 minutes at this temperature.

After the reaction, 4.5 g of 40% aqueous sodium hydroxide solution was added to the reaction mixture and the solvent was distilled out under reduced pressure. To the residue were added water and toluene to perform extraction and the aqueous layer was separated. This aqueous layer was neutralized with dilute sulfuric acid and extracted with toluene and then the organic layer was washed with water. Then, the organic layer was concentrated and thereafter distilled to obtain 4.8 g of a distillate having a boiling point of 110°–119° C./2.5 mmHg. The IR spectrum of the product showed that it was chrysanthemic acid. Gas chromatography assay gave the results: cis, 5.0% and trans, 95.0%.

EXAMPLE 31

5.0 g of cis-chrysanthemic acid and 59 mg of azobisisobutyronitrile were dissolved in 20 g of toluene. 0.35 g of 25% solution of hydrogen bromide in acetic acid was added dropwise to the solution with stirring at 80° C. and reaction was effected for 30 minutes.

Gas chromatography assay showed the composition: cis, 7.9% and trans, 92.1%.

EXAMPLE 32

12.8 g of ethyl chrysanthemate comprising cis, 35.0% and trans, 65.0% was dissolved in 100 g of dioxane. Then, thereto were added dropwise 0.25 g of t-butyl hydroperoxide and 0.56 g of phosphorus tribromide at 20° C. and stirring was carried out for 1 hour at this temperature.

After the reaction, the reaction mixture was neutralized with a 2% aqueous sodium hydroxide solution and then the solvent was distilled out under reduced pressure. To the residue were added hexane and 2% aqueous sodium hydroxide solution to carry out extraction and the organic layer was washed with water. The resulting organic layer was concentrated under reduced pressure and then distilled to obtain 11.7 g of a distillate having a boiling point of 85°-88° C./10 mmHg.

The IR spectrum of the product showed that it was ethyl ester of chrysanthemic acid. Gas chromatography assay showed the composition: cis, 3.9% and trans, 96.1%.

EXAMPLE 33

2.50 g of ethyl chrysanthemate comprising cis, 20% and trans, 80% was dissolved in 10 ml of dioxane and thereto was added 115 mg of t-butyl hydroperoxide. Then, thereto was added with stirring 410 mg of 25% solution of hydrogen bromide in acetic acid at room temperature.

After the reaction, the reaction mixture was neutralized with 2% aqueous sodium hydroxide solution and the solvent was distilled out under reduced pressure. To the residue were added hexane and 2% aqueous sodium hydroxide solution to effect extraction and the organic layer was washed with water. The resulting organic layer was concentrated under reduced pressure and then distilled to obtain 2.25 g of a distillate having a boiling point of 85°-88° C./10 mmHg.

The IR spectrum of the product showed that it was ethyl ester of chrysanthemic acid. Gas chromatography assay showed the composition: cis, 5.0% and trans, 95.0%.

We claim:

1. A method for the racemization of optically active chrysanthemic acid or its ester of the formula:

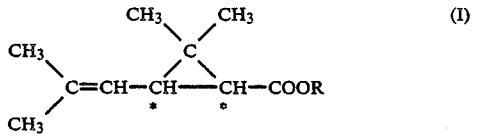

wherein R represents a hydrogen atom, an alkyl group of 1–20 carbon atoms, a cycloalkyl group of 3–20 carbon atoms or an aralkyl group of 7–20 carbon atoms and * mark represents an asymmetric carbon atom, which comprises contacting the acid or its ester with hydrogen bromide or a phosphorus bromide compound.

2. A method according to claim 1 which is carried out in the presence of a peroxide or an azo compound.

3. A method according to claim 1 or 2 wherein the phosphorus bromide compound is at least one compound selected from the group consisting of phosphorus tribromide, phosphorus pentabromide and phosphorus oxybromide.

4. A method according to claim 2 wherein the peroxide is at least one compound selected from the group consisting of hydroperoxides, diacyl peroxides, peroxy esters, ketone peroxides, dialkyl peroxides, peracids and hydrogen peroxide.

5. A method according to claim 2 wherein the peroxide is hydroperoxides, diacyl peroxides or peroxy esters.

6. A method according to claim 2 wherein the azo compound is at least one compound selected from the group consisting of azonitriles, azo esters and alkylazo compounds.

7. A method according to claim 2 wherein the azo compound is at least one compound selected from the group consisting of azonitriles and azo esters.

8. A method for conversion of cis isomer or of a mixture of cis and trans isomers of chrysanthemic acid or its ester of the formula:

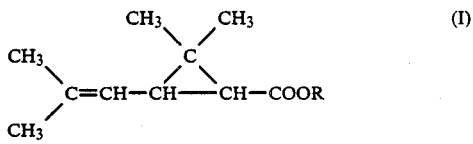

wherein R represents a hydrogen atom, an alkyl group of 1–20 carbon atoms, a cycloalkyl group of 3–20 carbon atoms or an aralkyl group of 7–20 carbon atoms, to the corresponding trans-rich chrysanthemic acid or its ester, which comprises contacting the acid or its ester described above with hydrogen bromide or a phosphorus bromide compound.

9. A method according to claim 8 which is carried out in the presence of a peroxide or an azo compound.

10. A method according to claim 8 or 9 wherein the phosphorus bromide compound is at least one compound selected from the group consisting of phosphorus tribromide, phosphorus pentabromide and phosphorus oxybromide.

11. A method according to claim 9 wherein the peroxide is at least one compound selected from the group consisting of hydroperoxides, diacyl peroxides, peroxy esters, ketone peroxides, dialkyl peroxides, peracids and hydrogen peroxide.

12. A method according to claim 9 wherein the peroxide is a member selected from the group consisting of hydroperoxides, diacyl peroxides or peroxy esters.

13. A method according to claim 9 wherein the azo compound is at least one compound selected from the group consisting of azonitriles, azo esters and alkylazo compounds.

14. A method according to claim 9 wherein the azo compound is at least one compound selected from the group consisting of azonitriles and azo esters.

15. A method according to claim 3 wherein the peroxide is at least one compound selected from the group consisting of hydroperoxides, diacyl peroxides, peroxy esters, ketone peroxides, dialkyl peroxides, peracids and hydrogen peroxide.

16. A method according to claim 3 wherein the peroxide is hydroperoxides, diacyl peroxides or peroxy esters.

17. A method according to claim 3 wherein the azo compound is at least one compound selected from the group consisting of azonitriles, azo esters and alkylazo compounds.

18. A method according to claim 3 wherein the azo compound is at least one compound selected from the group consisting of azonitriles and azo esters.

19. A method according to claim 1, wherein the optically active chrysanthemic acid or its ester is selected from the group consisting of chrysanthemic acid, methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

20. A method according to claim 8, wherein the optically active chrysanthemic acid or its ester is selected from the group consisting of chrysanthemic acid, methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

21. A method according to claim 1, wherein the hydrogen bromide or phosphorus bromide compound is used in an amount of $1/1000$–$\frac{1}{4}$ mole per mole of compound (I).

22. A method according to claim 8, wherein the hydrogen bromide or phosphorus bromide compound is used in an amount of $1/1000$–$\frac{1}{4}$ mole per mole of compound (I).

23. A method according to claim 2, wherein the hydrogen bromide or phosphorus bromide compound is used in an amount of $1/200$–$1/5$ mole per mole of compound (I).

24. A method according to claim 9, wherein the hydrogen bromide or phosphorus bromide compound is used in an amount of $1/200$–$1/5$ mole per mole of compound (I).

25. A method according to claim 2, wherein the peroxide is used in an amount of $1/20$–$5$ moles per mole of the hydrogen bromide or phosphorus bromide compound.

26. A method according to claim 9, wherein the peroxide is used in an amount of $1/20$–$5$ moles per mole of the hydrogen bromide or phosphorus bromide compound.

27. A method according to claim 2, wherein the azo compound is used in an amount of $1/10$ to $5$ moles per mole of the hydrogen bromide or phosphorus bromide compound.

28. A method according to claim 9, wherein the azo compound is used in an amount of $1/10$ to $5$ moles per mole of the hydrogen bromide or phosphorus bromide compound.

29. A method according to claim 1, wherein the reaction temperature is from $-70°$ to $100°$ C.

30. A method according to claim 8, wherein the reaction temperature is from $-70°$ to $100°$ C.

* * * * *